(12) United States Patent
Ling (10) Patent No.: US 12,111,236 B2
(45) Date of Patent: Oct. 8, 2024

(54) SAMPLE COLLECTION AND DETECTION DEVICE AND METHOD

(71) Applicant: Assure Tech. (Hangzhou) Co., Ltd, Zhejiang (CN)

(72) Inventor: Shi sheng Ling, Zhejiang (CN)

(73) Assignee: Assure Tech. (Hangzhou) Co., Ltd, Zhejiang (CN)

( * ) Notice: Subject to any disclaimer, the term of this patent is extended or adjusted under 35 U.S.C. 154(b) by 91 days.

(21) Appl. No.: 18/177,696

(22) Filed: Mar. 2, 2023

(65) Prior Publication Data

US 2023/0204468 A1 Jun. 29, 2023

Related U.S. Application Data

(62) Division of application No. 16/603,833, filed as application No. PCT/CN2018/079712 on Mar. 21, 2018, now Pat. No. 11,630,036.

(30) Foreign Application Priority Data

Apr. 13, 2017 (CN) .......................... 201710240475.1

(51) Int. Cl.
*B01L 3/00* (2006.01)
*G01N 1/14* (2006.01)

(52) U.S. Cl.
CPC ................ *G01N 1/14* (2013.01); *B01L 3/502* (2013.01); *B01L 2300/025* (2013.01); *B01L 2300/0663* (2013.01); *B01L 2300/069* (2013.01); *B01L 2300/0832* (2013.01)

(58) Field of Classification Search
CPC ............ A61B 10/0038; A61B 10/0051; A61B 10/007; B01L 3/502; B01L 3/5023; B01L 3/5029; B01L 2300/046; B01L 2300/069
See application file for complete search history.

(56) References Cited

U.S. PATENT DOCUMENTS

| | | | | |
|---|---|---|---|---|
| 5,091,316 A | * | 2/1992 | Monthony | C12M 45/22 600/572 |
| 5,376,337 A | * | 12/1994 | Seymour | A61B 10/0051 422/535 |
| 2003/0064526 A1 | * | 4/2003 | Niedbala | B01L 3/5029 600/584 |
| 2004/0184954 A1 | * | 9/2004 | Guo | B01L 3/5023 422/400 |
| 2004/0237674 A1 | * | 12/2004 | Wu | B01L 3/5029 73/864 |
| 2006/0057027 A1 | * | 3/2006 | Hudak | A61B 10/0051 422/549 |
| 2007/0208274 A1 | * | 9/2007 | Ostrowski | A61B 10/0045 600/572 |

* cited by examiner

*Primary Examiner* — Jill A Warden
*Assistant Examiner* — Dwayne K Handy
(74) *Attorney, Agent, or Firm* — JCIP GLOBAL INC.

(57) ABSTRACT

A sample collection and detection device includes a collection cavity. The device further includes a sample collector. The sample collector comprises a collection rod and an absorption element, and the absorption element has a hollow cavity. A part of the collection rod is received in the hollow cavity of the absorption element. A first lug for blocking and locating the absorption element is arranged on the collection rod. Also provided is a method for collecting and detecting sample using the sample collection and detection device.

5 Claims, 6 Drawing Sheets

SAMPLE COLLECTION AND DETECTION DEVICE AND METHOD

CROSS-REFERENCE TO RELATED APPLICATION

This application is a divisional application of U.S. application Ser. No. 16/603,833, filed on Oct. 9, 2019, which is a 371 of international application of PCT application serial no. PCT/CN2018/079712, filed on Mar. 21, 2018, which claims priority to and the benefit of China Patent Application No. 201710240475.1, filed on Apr. 13, 2017. The entirety of each of the above-mentioned patent applications is hereby incorporated by reference herein and made a part of this specification.

BACKGROUND

Technical Field

The present invention relates to a device and method for sample collection and detection, and in particular to a device and method for collecting and detecting a fluid sample by using a sample collector.

Description of Related Art

The following background art is used for helping readers to understand the present invention and cannot be considered as the prior art.

The technique of detecting whether an analyte exists in a sample by using the principle of immune conjugation reaction is widely used in various fields. It can be used for detecting the analytes in various biological samples (saliva, blood, urine, serum, sweat and the like) to monitor diseases and human health (early pregnancy, cancer, infectious diseases, drugs and the like). The fundamental principle of this detection technique is established basis on the specific binding performance between immune molecules, such as antibodies and antigens, haptens/antibodies, biotin and anti-biotin, and the like.

In the field of medical diagnosis, it is a relatively common method to use a detection device or a detection cup to collect and detect a liquid sample and to judge whether the liquid sample contains the analyte. Such a detection device or detection cup generally requires that the sample is collected in a sample container, and a relevant technical personnel inserts a detection reagent strip and immerses a part of the reagent strip in the sample, takes out the reagent strip after a few time and reads a detection result.

The U.S. Patent Publication No. 2004/0184954 and U.S. Patent Publication No. 2004/0237674 disclose some devices for collecting saliva and detecting whether the saliva contains illegal pharmaceutical ingredients. In both of the patents, devices and methods for collecting and detecting saliva are provided, in these devices, after the sample is sampled onto a collector, the sample in an absorption element on the collector is squeezed into a collection cavity by applying an external force, and then detection is performed.

In these devices, the collection of the sample on the collector is usually carried out by placing an adsorbing element of the collector in the oral cavity of a subject, the adsorbing elements of the existing collectors are bond and fixed to collection handles by glue, since the glue generates odor and also contains some chemical elements unfavorable to the human body, situations in which the subject is uncomfortable and enough sample amount cannot be collected due to the discomfort of the subject are generated frequently. In addition, the absorption elements of these existing collection and detection devices are generally placed in the collection cavities, pressure is applied to the handles to squeeze and compress the absorption elements via the collection cavities and the handles, so that the samples flow out from the absorption elements, which requires a large force to squeeze the collector, so that the sample on the collector is transferred into the collection device. This brings inconvenience for operators, and particularly female operators.

SUMMARY

The present invention provides a sample collector of a new structure, and a sample collection and detection device cooperating with the collector for use. In the new sample collector, an absorption element is connected or fixed by causing the absorption element to pass through a collection rod instead of bonding the absorption element with the collection rod by using glue, so that a subject is no longer in contact with the bonding glue, thus the use is safer. Furthermore, the new sample collection and detection device cooperating with the collector for use is easier, simpler, labor-saving and easier to be operated than the previous device.

The present invention provides a sample collector, including a collection rod and an absorption element, wherein the absorption element is provided with a hollow cavity; and a part of the collection rod is accommodated in the hollow cavity of the absorption element.

Since the part of the collection rod is accommodated in the hollow cavity of the absorption element, the collection rod is connected with the absorption element; that is, the absorption element is connected to one end of the collection rod, specifically, one end of the collection rod and the part of the collection rod above the end are accommodated in the hollow cavity of the absorption element, and meanwhile, the absorption element is entirely located on the collection rod.

In some preferred embodiments, in order to prevent the absorption element from easily sliding on the collection rod and ensure a tighter connection therebetween, the hollow cavity of the absorption element is in zero clearance fit with the collection rod. That is, the structure and the size of the hollow cavity of the absorption element are the same as the structure and the size of the collection rod, and an inner surface of the hollow cavity is in contact connection with an outer surface of the collection rod.

In some preferred embodiments, a first lug for blocking and locating the absorption element is arranged on the collection rod. The first lug is used for preventing the absorption element from further moving on the collection rod and meanwhile defining a position of the absorption element on the collection rod. In some embodiments, a position of the first lug on the collection rod corresponds to a length of the absorption element. Specifically, a distance between the first lug and one end of the collection rod is equal to or slightly greater than the length of the absorption element, and specifically, one end of the collection rod is a tail end of the collection rod.

In some preferred embodiments, the collector further includes a gasket; and the gasket has a through hole.

In some preferred embodiments, the through hole passes through the collection rod to connect the gasket to the collection rod; and the absorption element is located between the gasket and the first lug. The gasket is connected to the collection rod for defining and fixing the absorption element, so that the absorption element does not slip off from the collection rod and to further fix the position of the absorption element on the collection rod at the same time, that is, the absorption element is fixedly connected between the gasket and the first lug. More specifically, the gasket is connected to one end of the collection rod, and preferably, the gasket is connected to the tail end of the connecting rod.

In some preferred embodiments, in order to prevent components loaded on the collection rod from slipping off, an end part of one end of the collection rod connected with the absorption element is provided with engaging teeth, specifically, the end part of the tail end of the collection rod is provided with the engaging teeth, and the engaging teeth protrude from a surface of the collection rod. In some preferred embodiments, two engaging teeth are provided, and positions of the two engaging teeth are symmetrical. In some specific embodiments, the engaging teeth are of barb-shaped structures. The engaging teeth are arranged on one end of the collection rod connected with the absorption element for preventing the components (the absorption element and the gasket) on the collection rod from sliding off from the collection rod. Preferably, since the engaging teeth are fixed to one end of the collection rod, when the absorption element and the gasket are installed, it is necessary to pass through the engaging teeth at first to smoothly pass through the collection rod, and since the engaging teeth are of the barb-shaped structures, the absorption element and the gasket have no barrier to enter the tail end of the connecting rod.

In some preferred embodiments, the end part of one end of the collection rod connected with the absorption element is provided with a groove. Due to the arrangement of the groove, this end of the collection rod deforms toward an interior of the groove after being compressed, so that the components can be conveniently loaded on the collection rod, such as the absorption element and the gasket.

In a more preferred embodiment, the engaging teeth are located on both sides of the groove at the end part of the collection rod. That is, symmetrical engaging teeth are arranged on the both sides of the groove at the end part of the collection rod.

Preferably, the engaging teeth and the groove are located at the tail end of the collection rod.

In some preferred embodiments, the gasket is buckled at the engaging teeth at the end part of the collection rod. That is, portions of the engaging teeth protruding from the surface of the collection rod block the gasket to prevent the same from dropping off or sliding off from the collection rod.

In some preferred embodiments, a pore size of the through hole is the same as an outer diameter of the collection rod. That is to say, a gap between the through hole and the collection rod is zero, the gasket does not slide on the collection rod, and can only move up and down on the collection rod under an action of an external force.

In some preferred embodiments, the collection rod further includes a second lug; and the second lug is located between the other end of the collection rod and the first lug.

In some preferred embodiments, the other end of the collection rod is provided with a handle. The handle allows an operator to hold the collector for operation.

Preferably, the other end of the collection rod is a top end of the collection rod.

In another aspect, the present invention further provides a sample collection and detection device, including a collection cavity, wherein the device further includes a sample collector, the sample collector includes a collection rod and an absorption element, and the absorption element is provided with a hollow cavity; and a part of the collection rod is accommodated in the hollow cavity of the absorption element.

Since the part of the collection rod is accommodated in the hollow cavity of the absorption element, the collection rod is connected with the absorption element; that is, the absorption element is connected to one end of the collection rod, specifically, one end of the collection rod and the part of the collection rod above the end are accommodated in the hollow cavity of the absorption element, and meanwhile, the absorption element is entirely located on the collection rod.

In some preferred embodiments, in order to prevent the absorption element from easily sliding on the collection rod and ensure a tighter connection therebetween, the hollow cavity of the absorption element is in zero clearance fit with the collection rod. That is, the structure and the size of the hollow cavity of the absorption element are the same as the structure and the size of the collection rod, and an inner surface of the hollow cavity is in contact connection with an outer surface of the collection rod.

In some preferred embodiments, a first lug for blocking and locating the absorption element is arranged on the collection rod. The first lug is used for preventing the absorption element from further moving on the collection rod and meanwhile defining a position of the absorption element on the collection rod. In some embodiments, a position of the first lug on the collection rod corresponds to a length of the absorption element. Specifically, a distance between the first lug and one end of the collection rod is equal to or slightly greater than the length of the absorption element, and specifically, one end of the collection rod is a tail end of the collection rod.

In some preferred embodiments, the collection device further includes a gasket having a through hole; the through hole passes through the collection rod to connect the gasket to the collection rod; and the absorption element is located between the gasket and the first lug. More specifically, the gasket is connected to one end of the collection rod, and preferably, the gasket is connected to the tail end of the collection rod.

In some preferred embodiments, an end part of one end of the collection rod connected with the absorption element is provided with engaging teeth, and the engaging teeth protrude from a surface of the connecting rod; and the end part of one end of the collection rod connected with the absorption element is provided with a groove. Due to the arrangement of the groove, the tail end of the collection rod deforms toward an interior of the groove after being compressed, and the engaging teeth are used for preventing the components on the collection rod from sliding off.

In a more preferred embodiment, the gasket is buckled at the engaging teeth at the end part of the collection rod through the through hole.

In some preferred embodiments, a pore size of the through hole of the gasket is the same as an outer diameter of the collection rod.

In some preferred embodiments, the collection and detection device further includes an extrusion cylinder, and the extrusion cylinder is fixedly connected in the collection cavity.

In some preferred embodiments, a cylinder opening of the extrusion cylinder is provided with a platform. That is, the cylinder opening of the extrusion cylinder has a horizontal plane.

In a specific embodiment, the collection rod and the absorption element are cylindrical, and the extrusion cylinder is cylindrical, so that the platform is an annular plane surrounding the cylinder opening.

In some preferred embodiments, a height of the extrusion cylinder is greater than or equal to the length of the absorption element; and an inner diameter of the extrusion cylinder is greater than or equal to a diameter of the collection rod.

In the present invention, the liquid sample on the absorption element is extruded out by the cooperation of the extrusion cylinder and the sample collector, according to the structure of the sample collector provided by the present invention, the extrusion cylinder is designed to be able to compress the absorption element to cause the liquid sample therein to flow out and to enable the flowing out liquid sample to reach the collection cavity, therefore, the extrusion cylinder is located in the collection cavity at first, and specifically, the extrusion cylinder is fixed in the collection cavity; more specifically, a bottom portion of the extrusion cylinder is located in the collection cavity, and the two components are fixedly connected, and preferably, the bottom portion of the extrusion cylinder can also be a part of a bottom portion of the collection cavity; and in some other embodiments, the extrusion cylinder is close to one side of the collection cavity, and the platform at an opening of the extrusion cylinder is connected to a side wall of the collection cavity. Secondly, the extrusion cylinder accommodates the collection rod portion of the collector to block the absorption element at an outside of the extrusion cylinder so as to extrude the absorption element to allow liquid to flow out, therefore, an inner cavity of the extrusion cylinder need to accommodate the collection rod to block the absorption element, in this way, a shape of the inner cavity of the extrusion cylinder is the same as that of the absorption element, a size of the extrusion cylinder is also corresponding matched with that of the collection rod part, that is, the height of the extrusion cylinder is greater than or equal to the length of the absorption element; and the inner diameter of the extrusion cylinder is greater than or equal to the diameter of the collection rod, etc.

In some preferred embodiments, a diameter of the gasket is greater than the inner diameter of the extrusion cylinder. In this way, the gasket is blocked at the outside of the extrusion cylinder.

In some preferred embodiments, the sample collector is inserted into the collection cavity, at first, the absorption element on the collector is located directly above the extrusion cylinder; secondly, the collector continues to move in a direction of insertion into the extrusion cylinder, the collection rod located in the hollow cavity of the absorption element enters the extrusion cylinder, the gasket at a bottom portion of the absorption element is blocked and extruded by the cylinder opening platform of the extrusion cylinder, the absorption element is compressed after being extruded by the cylinder opening platform and the gasket, and the liquid flows onto the cylinder opening platform and a side wall of the extrusion cylinder after being extruded out from the absorption element; and finally, the absorption element of the collector is entirely compressed, and all liquid in the absorption element flows into the collection cavity along the cylinder opening platform and the side wall of the extrusion cylinder.

In the present invention, in a sample collection process, the collection rod part located in the absorption element enters the extrusion cylinder to fix a position between the extrusion cylinder and the collector, so that the absorption element is also fixed more stably relative to the platform of the extrusion cylinder; and meanwhile, since the absorption element is located on the collection rod between the first lug and the gasket in a surrounding manner, when the pressure is applied to the collector to extrude and compress the absorption element, since the position of the absorption element is fixed to the collection rod between the first lug on the cylinder opening platform and the gasket, the absorption element generates no position offset due to the external extrusion, such that the applied extrusion force is not dispersed and is entirely used for compressing the absorption element. Under normal conditions, in the existing collector, the absorption element is located at one end of the handle, in the compression process, since the absorption element has elasticity, the position of the absorption element changes when being compressed, and then the compression pressure is dispersed. Therefore, in the case that the same force is applied, the absorption element of the present invention has a better compression effect, more complete compression, and more sample outflow. Therefore, the present invention is more labor-saving and efficient by extruding the liquid sample in the absorption element via the cooperation of the extrusion cylinder and the collector.

In a more preferred embodiment, when the collection rod enters the extrusion cylinder, the engaging teeth on the end part of the collection rod enter the extrusion cylinder at first and are extruded by an inner side wall of the extrusion cylinder, and the end part of the collection rod deforms toward the groove, so that the end part of the collection rod enters the extrusion cylinder; and accordingly, the collection rod enters the extrusion cylinder.

In some preferred embodiments, after the absorption element is fully compressed, the collection rod is fixed in the extrusion cylinder by the engaging teeth. After the collection rod is fixed in the collection cavity, the collector will not be discarded separately, resulting in subsequent environmental pollution, thereby being more environmentally friendly.

In some other preferred embodiments, after the absorption element is fully compressed, the tail end of the collection rod reaches the bottom of the extrusion cylinder.

In some preferred embodiments, the collection cavity further includes an engaging cover for receiving and fixing the sample collector, and the engaging cover is fixed at the cavity opening of the collection cavity.

In some preferred embodiments, the engaging cover has an opening for receiving the sample collector, and a position of the opening corresponds to a position of the extrusion cylinder; and the collector is located directly above the cylinder opening of the extrusion cylinder after entering the opening of the engaging cover.

In some preferred embodiments, an inner wall of the engaging cover is provided with an annular projection; the collection rod is provided with a second lug, and the second lug is located between the other end of the collection rod and the first lug; and when the second lug reaches the annular projection, the collector is prevented from continuing to enter the collection cavity.

In some preferred embodiments, the device further includes a detection cavity, and the detection cavity is in liquid communication with the collection cavity.

In some preferred embodiments, a side wall of one side of the extrusion cylinder close to the detection cavity is provided with a flow guide slope. The flow guide slope can gather more liquid samples on an outer side wall of the extrusion cylinder, thus allowing more samples to quickly flow into the detection cavity through the flow guide slope, and thus the detection is faster and effective.

In some preferred embodiments, the device further includes a test element, and the test element is located in the detection cavity.

In the present invention, a sample collection and detection method for a sample collection and detection device is further provided. The device includes a collection cavity, an extrusion cylinder located in the collection cavity, a test element and a sample collector; the test element is in liquid communication with the collection cavity. The method includes following steps.

Collecting a sample by using the collector to fill the collector with the liquid sample.

Inserting the collector filled with the liquid sample into the extrusion cylinder in the collection cavity, so that the sample flows into the collection cavity.

Causing the sample in the collection cavity to flow into the test element for detection.

Reading a detection result on the test element.

Preferably, the sample collector includes a collection rod and an absorption element, and the absorption element is provided with a hollow cavity; a part of the collection rod is accommodated in the hollow cavity of the absorption element; a first lug for blocking and locating the absorption element is arranged on the collection rod; the collector further includes a gasket having a through hole, and the through hole passes through the collection rod to connect the gasket to one end of the collection rod; the absorption element is located between the gasket and the first lug; a cylinder opening of the extrusion cylinder is provided with a platform; an inner diameter of the extrusion cylinder is greater than or equal to a diameter of the collection rod and is less than a diameter of the gasket.

When the collector collects the sample, the absorption element is filled with the liquid sample.

After the collector is inserted into the collection cavity, the absorption element on the collector is located directly above the cylinder opening of the extrusion cylinder at first.

The collector is caused to continue to move in a direction of insertion into the extrusion cylinder, the collection rod located in the hollow cavity of the absorption element enters the extrusion cylinder, the gasket at a bottom portion of the absorption element is blocked by the cylinder opening platform of the extrusion cylinder, the absorption element is compressed after being extruded by the cylinder opening platform and the gasket, and liquid flows onto the cylinder opening platform and a side wall of the extrusion cylinder after being extruded out from the absorption element.

Preferably, a height of the extrusion cylinder is greater than or equal to a length of the absorption element.

The absorption element of the collector is fully compressed, and all the liquid in the absorption element flows into the collection cavity along the cylinder opening platform and the side wall of the extrusion cylinder.

Preferably, the end part of one end of the collection rod connected with the absorption element is provided with engaging teeth, and the engaging teeth protrude from the surface of the collection rod; and the end part of one end of the collection rod connected with the absorption element is provided with a groove.

The collector continues to move in the direction of insertion into the extrusion cylinder, the engaging teeth on the end part of the collection rod enter the extrusion cylinder and are extruded by an inner side wall of the extrusion cylinder, and the end part of the collection rod deforms toward the groove, so that the end part of the collection rod enters the extrusion cylinder, and accordingly, the collection rod enters the extrusion cylinder.

After the absorption element is fully compressed, the end part of one end of the collection rod connected with the absorption element reaches a bottom portion of the extrusion cylinder, and the collection rod is fixed in the extrusion cylinder by the engaging teeth.

Preferably, the device further includes a detection cavity, and the detection cavity is in liquid communication with the collection cavity; and the test element is located in the detection cavity.

Preferably, the device further includes an engaging cover, and the engaging cover is covered and fixed at the cavity opening of the collection cavity; the engaging cover is provided an opening, and a position of the opening corresponds to a position of the extrusion cylinder; the engaging cover is provided an annular projection, the collection rod is provided with a second lug, and the second lug is located between the first lug and the other end of the collection rod.

The collector is located directly above the cylinder opening of the extrusion cylinder after being inserted into the opening of the engaging cover.

When the second lug reaches the annular projection, the absorption element is fully compressed, and the collector is prevented from continuing to enter the collection cavity.

Beneficial Effects

The sample collector, the sample collection and detection device, and the collection and detection method provided by the present invention are more environmentally friendly and safer, are more easily accepted by the subject, are simple and labor-saving to be used, and facilitate the detection of the subject.

DESCRIPTION OF THE EMBODIMENTS

The structure involved in the present invention or the technical terms used therein will be further described below.

Detection

Detection indicates to check or test whether a substance or material exists, such as, but not limited to, chemical substances, organic compounds, inorganic compounds, metabolites, drugs or drug metabolites, organic tissues or metabolites of organic tissues, nucleic acids, protein or polymers. In addition, the detection indicates to test the amount of the substance or material. Further, the detection further indicates immunodetection, chemical detection, enzyme detection, and the like.

Sample

The samples involved in the present invention refer to those substances which can be used for detecting, checking or diagnosing whether an analyte of interest exists. The sample can be, for example, a liquid sample, the liquid sample can include blood, plasma, serum, urine, saliva and various exudates, and can also include a liquid solution formed by pre-treating a solid sample and a semi-solid sample. The collected sample can be used for detecting whether the analyte exists by using the immunodetection, chemical detection, enzyme detection and other methods. In a preferred embodiment, the sample of the present invention is a saliva sample.

Analyte

Any analyte can be analyzed by using the device and method of the present invention. The analyte can be detected in any liquid or liquid sample, such as urine, saliva, saliva, blood, plasma, or serum.

The analyte can also be some hapten substances, including drugs (such as drugs of abuse). "Drugs of Abuse" (DOA) refers to the use of drugs in non-medical destinations (usually playing the role of paralysis). The device can also be used for detecting tests that are medically useful but are easily overdose, such as tricyclic antidepressants (imipramine or analogues) and acetaminophen. These drugs are decomposed into different small molecules after being absorbed by the human body, but these small molecules exist in body fluid, such as blood, urine, saliva, sweat or the like, or the small molecules exist in a part of the body fluid.

Test Element 500

A test element 500 can be a laterally flowing test paper strip that can detect a plurality of analytes. Of course, other suitable test elements can also be utilized in the present invention. Various test elements can be combined to be used in the present invention. One form is test paper. The test paper for analyzing the analyte (such as drugs or metabolites indicating physical conditions) in the sample can be in various forms, for example, in the form of immunoassay or chemical assays. The test paper can adopt an analysis mode of a non-competitive method or a competitive method. The test paper contains a water absorbing material having a sample receiving area, a reagent area and a test area. The sample is added to the sample receiving area and flows to the reagent area via the capillary action. In the reagent area, if the analyte exists, the sample is combined with the reagent. Then, the sample continues to flow to the detection area. Some other reagents, such as molecules that are specifically bound to the analyte, are immobilized in the detection area. These reagents react with the analyte (if present) in the sample and bind the analyte to the area, or bind with a certain reagent in the reagent area. A marker for displaying a detection signal exists in the reagent area or in a separate marking area.

A typical non-competitive method analysis mode is that, if the sample contains the analyte, the signal is generated, and if the sample contains no analyte, no signal is generated. In the competitive method, if the analyte does not exist in the sample, the signal is generated, and if the analyte exists, no signal is generated.

The test element 500 is test paper, which can be made of a material that absorbs water or does not absorb water. The test paper can include a variety of materials for liquid sample transfer. The material of one piece of test paper can be covered on another material, for example, a piece of filter paper is covered on a nitrocellulose membrane. One area of the test paper can be made of one or more materials, and the other area is made of one or more other materials. The test paper can be adhered to a certain supporting object or a hard surface for improving the strength of gripping the test paper. The analyte is detected by a signal generating system, for example, a composition of one or more signal generating systems is fixed in an analyte detection area of the test paper by using one or more enzymes that specifically react with the analyte, and using one or more methods of fixing the specific composition on the test paper. The substance generating the signal can be on the sample receiving area 201, the reagent area, or the detection area, or the entire test paper, and one or more materials of the test paper can be filled with the substance. A solution containing the signal substance is added to the surface of the test paper or one or more materials of the test paper are immersed in the solution containing the signal substance. The test paper with the added solution containing the signal substance is dried.

The various areas of the test paper can be arranged in the following manner. The sample receiving area, the reagent area, the detection area and a control area, an area determining whether the sample is adulterated, and a liquid sample absorption area. The control area is located behind the detection area. All areas can be arranged on a piece of test paper using only one material. Different areas can also be made of different materials. The areas can be in direct contact with the liquid sample, or different areas can be arranged according to a flow direction of the liquid sample, the tail end of each is connected and overlapped with the front end of the other area. The used material can be a material with good water absorption such as filter paper, a glass fiber or nitrocellulose membrane. The test paper can also take other forms Detection Cavity 400

A detection cavity 400 is typically a cavity for accommodating the test element 500 and enabling the liquid sample to enter the cavity to contact with the test element for detection. The shape thereof is varied and can be designed according to the shape and the number of the test elements that need to be accommodated. In the present invention, the test element is a test strip, therefore, in one embodiment, the detection cavity is of a plate structure having a bottom plate and an upper plate, the bottom plate and the upper plate are combined together in a clamping manner to form a cavity, more specifically, the bottom plate is provided with one or more protruding strip-shaped necks, and these necks are used for placing and fixing the test strip 500. In some other preferred embodiments, the upper plate is provided with a window, and a position of the window corresponds to the detection area of the test strip, so that the test result of the test strip can be conveniently observed.

In the following detailed description, reference characters carried in the drawings are a part of the description, which is illustrated by way of illustration of a particular specific solution of the present invention. It is not excluded that the present invention can also be practiced by other specific solutions and the structure of the present invention is changed without departing from the application range of the present invention.

Figure 1:
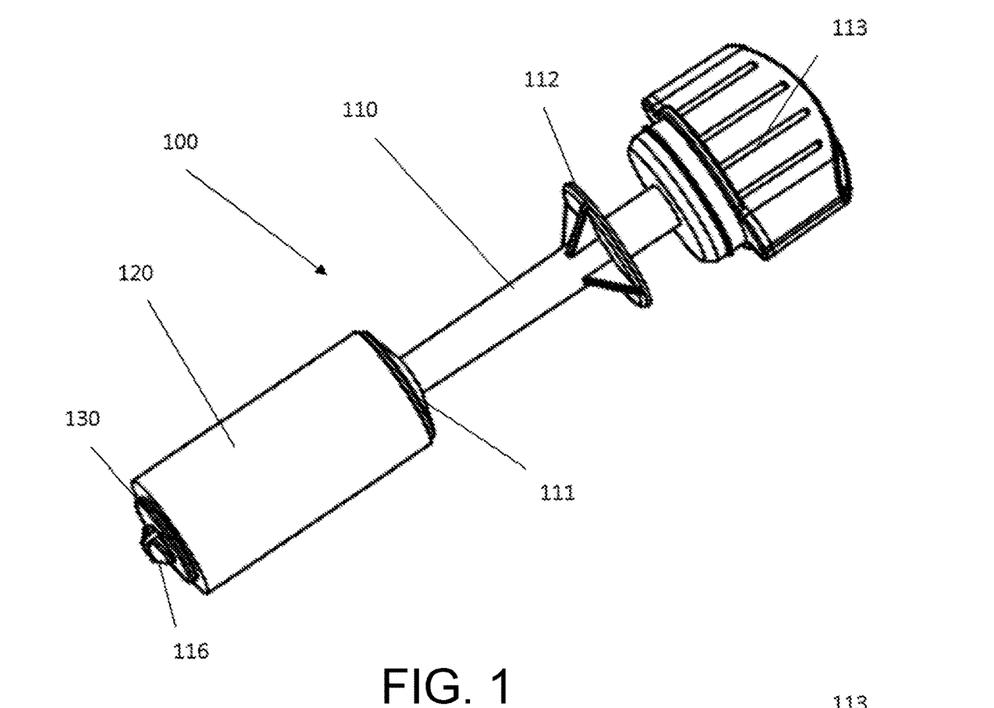
FIG. 1 is a schematic diagram of a collector of the present invention.
Figure 2:
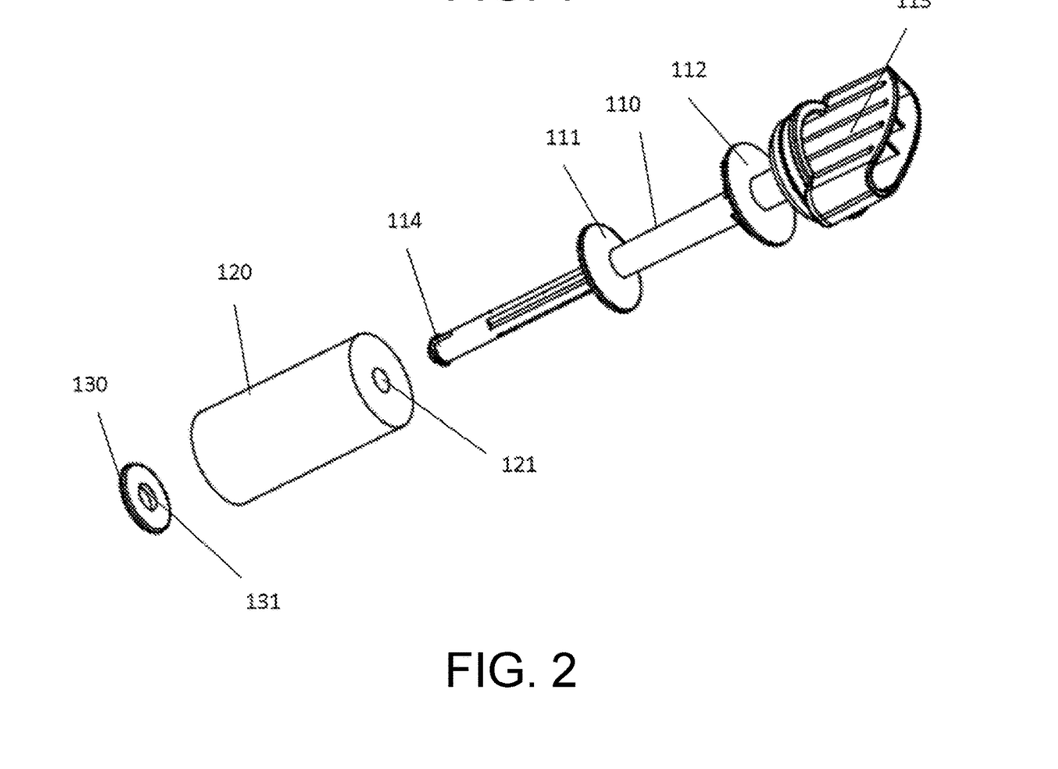
FIG. 2 is a decomposed schematic diagram of the collector of the present invention.

In the present invention, as shown in FIG. 1 and FIG. 2, a sample collector 100 includes an absorption element 120 and a collection rod 110, the absorption element 120 is provided with a hollow cavity 121, and a part of the collection rod 110 is accommodated in the hollow cavity 121 of the absorption element. For example, one end of the collection rod 110 is accommodated in the hollow cavity 121 of the absorption element, so that the collection rod 110 is connected with the absorption element 120. In a specific embodiment, the collection rod 110 has two ends, a top end 113 and a tail end 114, and the absorption element 120 is connected to the tail end 114 of the collection rod 110. More specifically, in order to ensure a tighter connection between the absorption element 120 and the collection rod 110, the structure and the size of the hollow cavity 121 of the absorption element are the same as the structure and the size of the part of the collection rod 120 inserted into the hollow cavity. The absorption element 120 is typically made of a medical grade sponge or foam material commonly used in the art. However, many other materials can also be made into the absorption element 120, such as cotton or paper, or any other material having water absorbing properties. The collection rod 110 is generally rigid, which is conducive to operating the absorption element 120. The collection rod 110 can be made of materials commonly used in the art, such as plastic, wood, metal or cardboard. The shapes of the absorption element 120 and the collection rod 110 are not limited, for example, the absorption element 120 can be spherical, elongated, cylindrical or the like, and the collection rod 110 can be cylindrical, rectangular, conical or the like. In some specific embodiments, the collection rod 110 and the absorption element 120 are both of cylindrical structures, and the hollow cavity 121 of the absorption element is also a cylindrical hollow cavity.

In order to define a position of the absorption element 120 connected to the collection rod 110, the collection rod 110 is provided with a first lug 111. The first lug 111 is fixed to the collection rod 110 for blocking the absorption element 120 from further moving to the top end of the collection rod on the collection rod 110. Generally, a position of the first lug 111 on the collection rod 110 corresponds to a length of the absorption element 120. Specifically, a distance between the first lug 111 and the tail end 114 of the collection rod is equal to or slightly greater than the length of the absorption element 120. That is, after the tail end 114 of the collection rod is inserted into the hollow cavity 121 of the absorption element, the absorption element 120 moves along the tail end 114 of the collection rod toward a direction of the top end on the collection rod 110 and is blocked after reaching the first lug 111, at this time, the absorption element 120 is completely located on the collection rod 110, and the tail end 114 of the collection rod is just located at an edge of a bottom portion of the absorption element 120 (the tail end 114 slightly protrudes from the edge of the bottom portion of the absorption element 120). A gasket 130 is installed on the tail end 114 of the collection rod and is adjacent to or in contact with the edge of the bottom portion of the absorption element 120, in a preferred embodiment, the gasket 130 is in contact with the edge of the bottom portion of the absorption element 120. At this time, the absorption element 120 is defined between the first lug 111 of the collection rod 110 and the gasket 130. More specifically, a top portion of the absorption element 120 is in contact with the first lug 111, and the bottom portion of the absorption element 120 is in contact with the gasket 130. The gasket 130 is provided with a through hole 131, and the tail end 114 of the collection rod passes through the through hole to connect the gasket 130 to the collection rod 110. Specifically, a pore size of the through hole 131 is the same as an outer diameter of the collection rod 110. That is to say, a gap between the through hole 131 and the collection rod 110 is zero, the gasket 130 does not slide on the collection rod 110, and can only move up and down on the collection rod 110 under an action of an external force. The material of the gasket 130 usually requires certain rigidity, the gasket can be made of materials commonly used in the art, such as plastic, wood, metal or cardboard. In a specific embodiment, the gasket 130 is of a circular structure.

Figure 3:
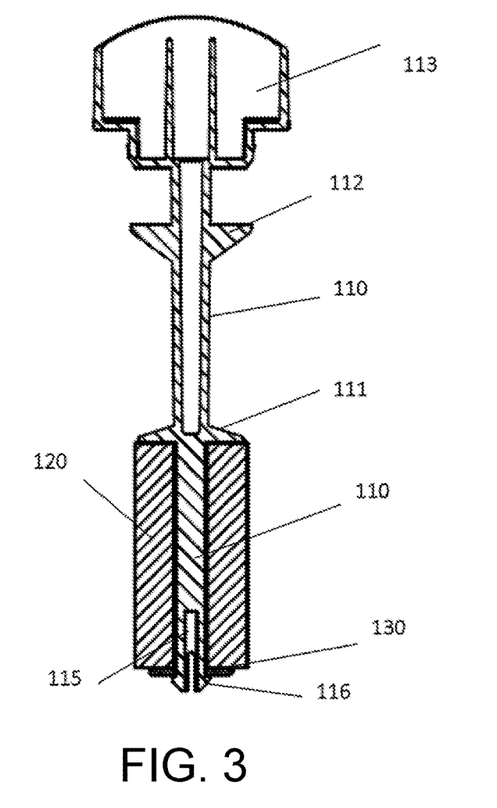
FIG. 3 is a sectional schematic diagram of the collector of the present invention.
Figure 4:
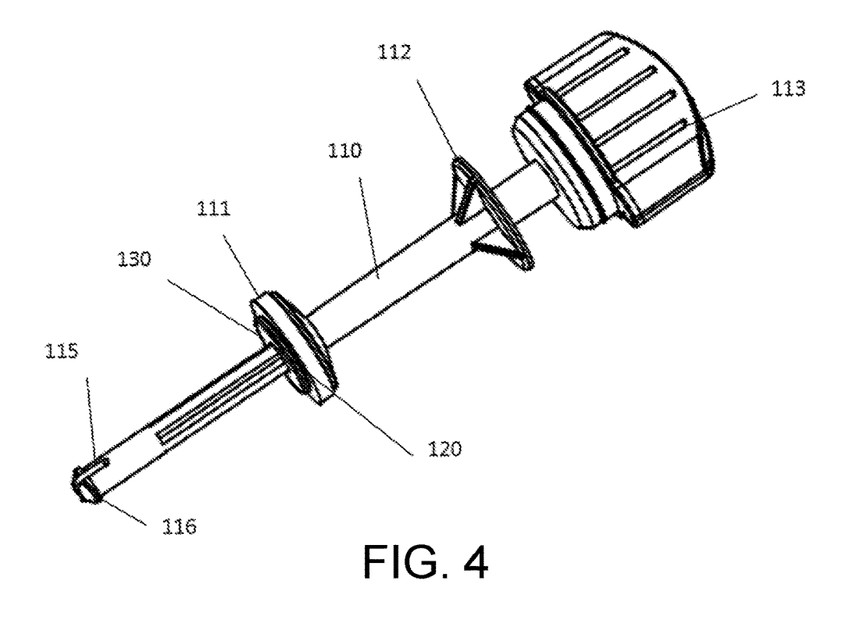
FIG. 4 is a schematic diagram of the collector of the present invention after an absorption element is compressed.
Figure 5:
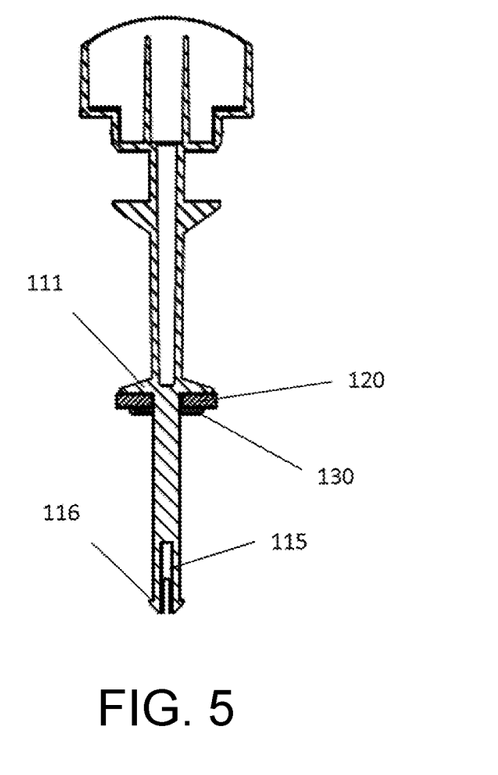
FIG. 5 is a sectional schematic diagram of the collector of the present invention after the absorption element is compressed.

In some embodiments, in order to prevent the absorption element 120 and the gasket 130 from slipping off from the collection rod 110, an end part of the tail end 114 of the collection rod is provided with engaging teeth 116, as shown in FIG. 4, the engaging teeth 116 protrude from a surface of the collection rod 100. In this way, the gasket 130 and the absorption element 120 are located on the engaging teeth. In a specific embodiment, one or more engaging teeth 116 can be provided and are distributed on the end part of the tail end 114 of the collection rod, and in one embodiment, two engaging teeth 116 are symmetrically distributed on a side wall of the end part of the tail end 114 of the collection rod. The shape of the engaging teeth 116 preferably selected in such a way that the components can be conveniently installed on the collection rod, and in some embodiments, the engaging teeth 116 are of barb-shaped structures. In some other embodiments, in order to conveniently install the components on the collection rod 110, the inserted end of the collection rod 110, that is, the tail end of the collection rod, can generate telescopic deformation, particularly, when the tail end is provided with the engaging teeth, the deformation is more advantageous, a groove 115 is formed in the tail end of the collection rod, as shown in FIG. 3, when an external force is applied to the tail end, the tail end deforms toward an interior of the groove 116, therefore the entire volume of the tail end 114 becomes smaller, so that the collection rod 110 can be conveniently inserted into the absorption element 120 and the gasket 130. In a specific embodiment, the engaging teeth 116 are symmetrically located on two side walls of the groove 115 in the tail end, as shown in FIG. 5.

Generally, the collection rod is further provided with a second lug 112, the second lug 112 is generally combined with the sample collection device for fixing the collector 100, and the second lug 112 is located between the top end of the collection rod and the first lug 111. In some embodiment, the size of the second lug 112 is greater than that of the first lug 111. In this way, when the sample collector 100 enters the collection device 800 to collect the sample, it can be ensured that the first lug 111 enters the collection device and is blocked by the second lug 112. In some embodiments, the top end of the collection rod is provided with a handle 113 for the convenient griping of the operator.

Figure 6:
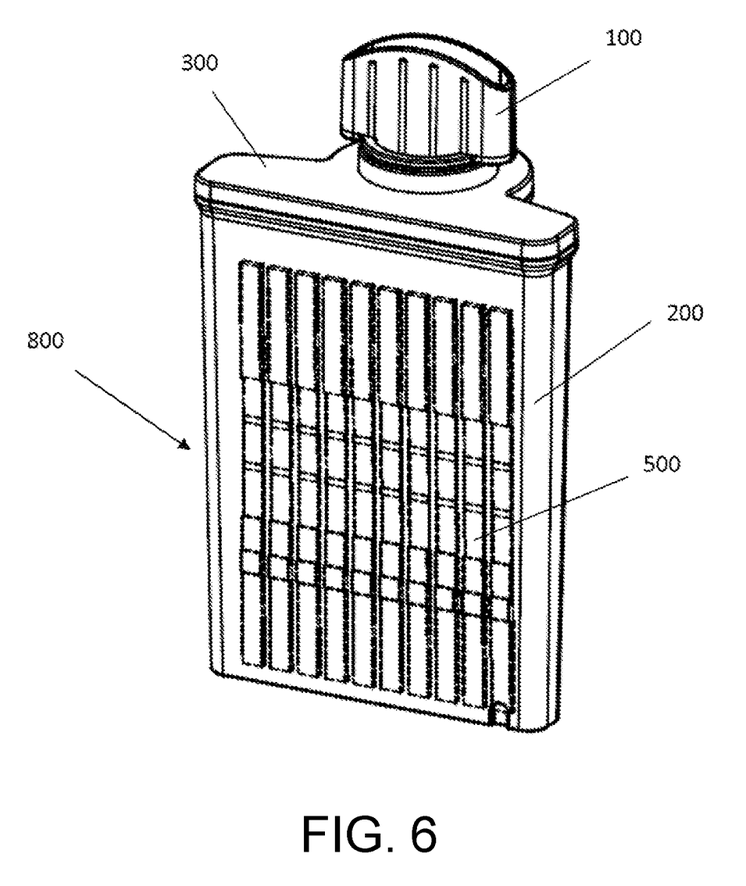
FIG. 6 is a schematic diagram of a collection and detection device of the present invention.
Figure 7:
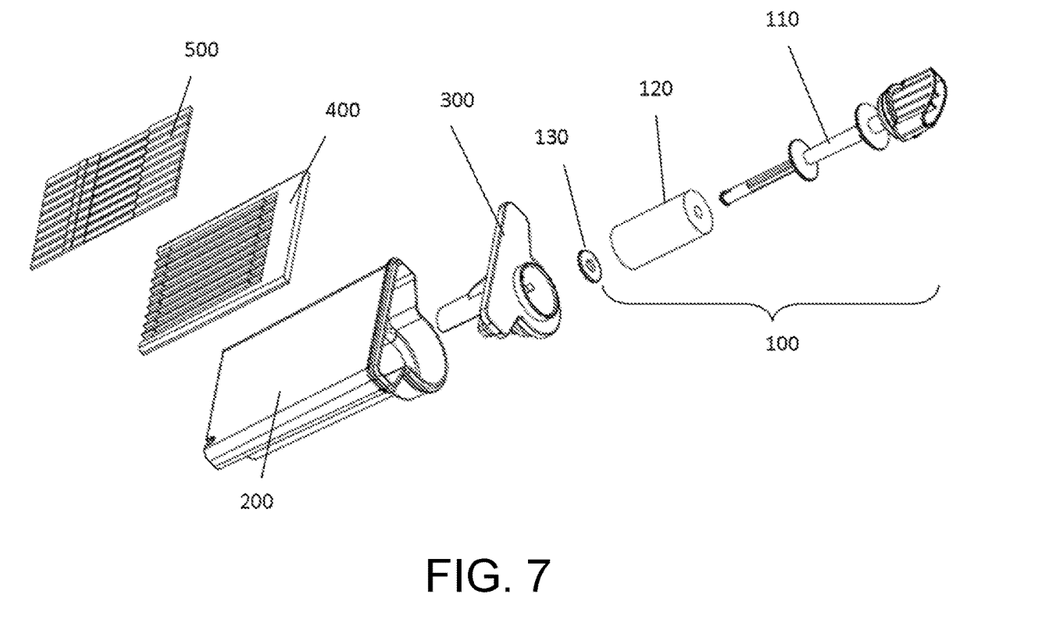
FIG. 7 is a decomposed schematic diagram of the collection and detection device of the present invention.
Figure 8:
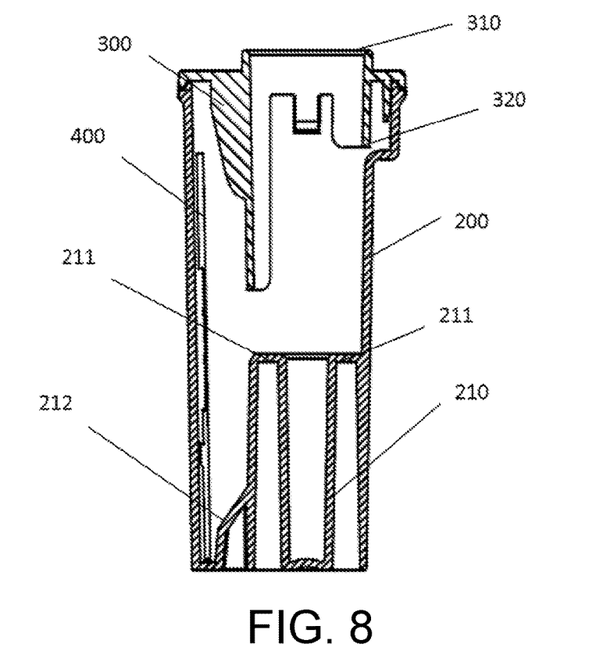
FIG. 8 is a sectional schematic diagram of a collection cavity of the collection and detection device of the present invention.

In the present invention, the sample collection and detection device 800 capable of accommodating the sample collector of the present invention includes a collection cavity 200 and a sample collector 100, and as shown in FIG. 6, a detection cavity 400 is further disposed on one side in the collection cavity 200. An extrusion cylinder 210 is further disposed in the collection cavity 200, the extrusion cylinder 210 is fixed in the collection cavity 200, as shown in FIG. 8, in a specific embodiment, the extrusion cylinder 210 is located on one side in the collection cavity 200, and a cylinder opening platform 211 of the extrusion cylinder is connected to an inner side wall of the collection cavity 200. An annular platform is formed around a cylinder opening. The collection cavity 200 is typically a cavity for accommodating the liquid sample, and capable of accommodating the test element and a structure for mounting the test element or the like. In some embodiments, a structure for causing the sample to flow into the collection cavity is further disposed in the collection cavity. Or, the collection cavity is further provided with a passage in fluid communication with the test element. The shape thereof is varied and can be designed according to functions needing to be achieved. In the embodiment of the present invention, as shown in FIG. 6 and FIG. 7, the collection cavity 200 is formed by enclosing a side wall plane on one surface and arc-shaped side walls on the rest surfaces on a bottom wall. The detection cavity 400 is further disposed on the other side in the collection cavity 200, and the test element 500 is installed in the detection cavity 400. A side wall of one side of the extrusion cylinder 210 close to the detection cavity 400 is provided with a flow guide slope 212 for quickly guiding liquid on the side wall to flow to the detection cavity 400. The extrusion cylinder 210 is used for cooperating with the collector 100 to collect the sample in the absorption element, and the extrusion cylinder 210 is used for accommodating the collection rod 110 in the hollow cavity 121 of the absorption element to prevent the absorption element 120 from entering, therefore, the height of the extrusion cylinder 210 is greater than or equal to the length of the absorption element 120 to ensure that a part of collection rod accommodated by the absorption element is accommodated. An inner diameter of the extrusion cylinder 210 is greater than or equal to a diameter of the collection rod 110 to ensure that the collection rod 110 can be inserted into the extrusion cylinder 210. At the same time, a diameter of the gasket 130 is greater than the inner diameter of the extrusion cylinder 210, so that the gasket 130 is blocked at an outside of the extrusion cylinder 210 and becomes a hard bottom for extruding the absorption element 120, and accordingly, the absorption element 120 can be compressed more easily.

The device 800 further includes an engaging cover 300 for receiving and fixing the sample collector, as shown in FIG. 7 and FIG. 8, the engaging cover 300 covers the cavity opening of the collection cavity 200 for sealing the same, specifically, the engaging cover 300 is buckled at the cavity opening of the collection cavity 200 to fix the collection cavity with the engaging cover, specifically, the engaging cover is provided with a neck for accommodating the cavity opening of the collection cavity 200, and the neck is buckled on a side wall of the cavity opening. The engaging cover 300 is provided with an opening 310, and a position of the opening 310 corresponds to a position of the extrusion cylinder 210 in the collection cavity, that is, a center of the opening 310 is overlapped with a center of the extrusion cylinder 210. When the collector 100 enters the collection cavity 200 through the opening 310 of the engaging cover, the absorption element 120 at a bottom portion of the collector is located directly above the cylinder opening of the collection cylinder 210. The engaging cover 300 is provided an annular projection 320, and the annular projection 320 protrudes toward an interior of the engaging cover 300. The projection 320 blocks the second lug 112 on the collector, so that the collector 100 cannot continue to enter the collection cavity 200 or the extrusion cylinder 210.

A sample collection and detection method will be specifically described below with respect to the sample collector 100 and the sample collection and detection device 800 of the present invention in conjunction with FIG. 9. Details are as follows.

The sample collector 100 is installed, the hollow cavity 121 of the absorption element 120 is inserted into the collection rod 110 by aligning with the tail end 114 of the collection rod having the engaging teeth 116 and the groove 115, until the absorption element 120 reaches the first lug 111. The through hole 131 of the gasket 130 is inserted into the collection rod 110 by aligning the tail end 114 of the collection rod, and the gasket 130 is located at the engaging teeth 116.

The sample collector 100 is placed in the oral cavity of a subject (or liquid to be sampled) to collect the sample, and the absorption element 120 is filled with the sample.

The collector 100 filled with the liquid sample is inserted into the opening 310 of the engaging cover 300 on the collection cavity 200, and the absorption element 120 on the collector is located directly above the cylinder opening of the extrusion cylinder 210.

The collector 100 continues to move in the direction of insertion into the extrusion cylinder 210, the collection rod 110 located in the hollow cavity of the absorption element enters the extrusion cylinder 210, that is, the engaging teeth 116 at the tail end of the collection rod enter the extrusion cylinder 210 to be extruded by an inner side wall of the extrusion cylinder 210, so that the tail end 114 of the collection rod deforms toward the groove 115, then tail end 114 of the collection rod enters the extrusion cylinder 210, and accordingly, the collection rod 100 enters the extrusion cylinder 210.

Meanwhile, the gasket 130 at the bottom portion of the absorption element is blocked and extruded by the cylinder opening platform 211 of the extrusion cylinder 210, the absorption element 120 is compressed after being extruded by the cylinder opening platform 211 and the gasket 130, and the liquid flows onto the cylinder opening platform 211 and the side wall of the extrusion cylinder 210 after being extruded out from the absorption element 120.

When the second lug 112 reaches the annular projection 320, the absorption element 120 of the collector is fully compressed, and all liquid in the absorption element 120 flows into the collection cavity 200 along the cylinder opening platform 211 and the side wall of the extrusion cylinder 210.

Figure 9:
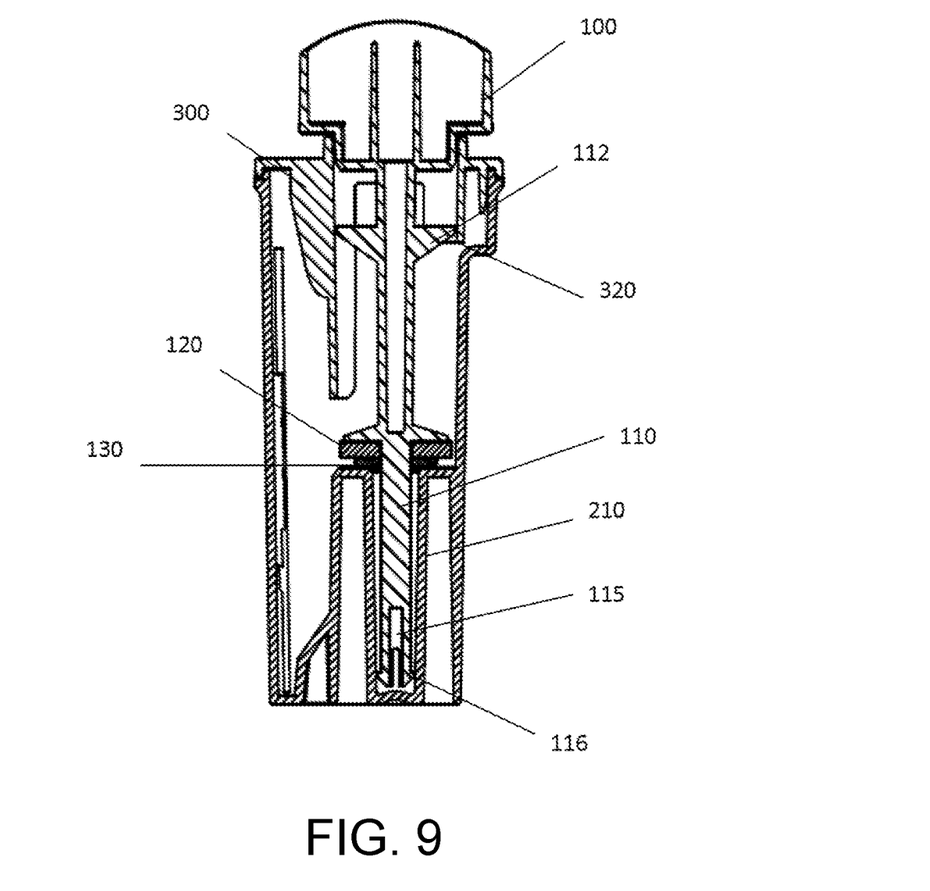
FIG. 9 is a sectional schematic diagram of the collection and detection device of the present invention after a sample is collected.

At the same time, the tail end 114 of the collection rod reaches the bottom portion of the extrusion cylinder 210, the collection rod 110 is fixed in the extrusion cylinder 210 by the engaging teeth 116, and the collector 100 is prevented from continuing to enter the collection cavity 200, as shown in FIG. 9.

The sample flowing to the cylinder opening platform 211 and the side wall of the extrusion cylinder 210 flows into the collection cavity 200 in a vicinity of the detection cavity 400 along the flow guide slope 212, and then flows into the detection cavity 400 to contact with the detection cavity 400 for detection.

A detection result on the test element is read.

What is claimed is:

1. A sample collection and detection method for a sample collection and detection device, wherein the sample collection and detection device includes a collection cavity, an extrusion cylinder located in the collection cavity, a test element and a sample collector; the test element is in liquid communication with the collection cavity; the sample collector includes a collection rod and an absorption element, and the absorption element is provided with a hollow cavity; a part of the collection rod is accommodated in the hollow cavity of the absorption element; a first lug for blocking and locating the absorption element is arranged on the collection rod; the sample collector further includes a gasket having a through hole, and the collection rod passes through the through hole to connect the gasket to one end of the collection rod; the absorption element is located between the gasket and the first lug; a cylinder opening of the extrusion cylinder is provided with a cylinder opening platform; an inner diameter of the extrusion cylinder is greater than or equal to a diameter of the collection rod and is less than a diameter of the gasket; wherein the sample collection and detection method comprising following steps:
- collecting a sample by using the sample collector to fill the absorption element of the sample collector with liquid sample;
- inserting the sample collector filled with the liquid sample into the extrusion cylinder in the collection cavity, so that the sample flows into the collection cavity;
- firstly locating the absorption element on the sample collector directly above the cylinder opening of the extrusion cylinder;
- then causing the sample collector to continue to move in a direction of insertion into the extrusion cylinder, causing the collection rod located in the hollow cavity of the absorption element to enter the extrusion cylinder, blocking the gasket at a bottom portion of the absorption element via the cylinder opening platform of the extrusion cylinder, compressing the absorption element after extruding the same via the cylinder opening platform and the gasket, flowing, by the liquid sample, onto the cylinder opening platform and a side wall of the extrusion cylinder after being extruded out from the absorption element, and flowing, by the liquid sample, into the collection cavity;
- causing the liquid sample in the collection cavity to flow into the test element for detection; and
- reading a detection result on the test element.

2. The sample collection and detection method according to claim 1, wherein a height of the extrusion cylinder is greater than or equal to a length of the absorption element; wherein:
- the collection rod accommodated in the absorption element completely enter the collection cylinder, the absorption element is fully compressed, and all the liquid in the absorption element flows into the collection cavity along the cylinder opening platform and the side wall of the extrusion cylinder.

3. The sample collection and detection method according to claim 2, wherein an end part of one end of the collection rod connected with the absorption element is provided with engaging teeth, and the engaging teeth protrude from a surface of the collection rod; and the end part of one end of the collection rod connected with the absorption element is provided with a groove; wherein:
- the sample collector continues to move along the direction of insertion into the extrusion cylinder, the engaging teeth on the end part of the collection rod enter the extrusion cylinder and are extruded by an inner side wall of the extrusion cylinder, and the end part of the collection rod deforms toward the groove, so that the end part of the collection rod enters the extrusion cylinder, and accordingly, the collection rod enters the extrusion cylinder; and
- after the absorption element is fully compressed, the end part of one end of the collection rod connected with the absorption element reaches a bottom portion of the extrusion cylinder, and the collection rod is fixed in the extrusion cylinder by the engaging teeth.

4. The sample collection and detection method according to claim 1, wherein the sample collection and detection device further comprises a detection cavity, and the detection cavity is in liquid communication with the collection cavity; and the test element is located in the detection cavity.

5. The sample collection and detection method according to claim 1, wherein the sample collection and detection device further comprises an engaging cover, and the engaging cover is covered and fixed at a cavity opening of the collection cavity; the engaging cover is provided an opening, and a position of the opening corresponds to a position of the extrusion cylinder; the engaging cover is provided an annular projection, the collection rod is provided with a second lug, and the second lug is located between the first lug and the other end of the collection rod; wherein:
- the sample collector is located directly above the cylinder opening of the extrusion cylinder after being inserted into the opening of the engaging cover; and
- when the second lug reaches the annular projection, the absorption element is fully compressed, and the sample collector is prevented from continuing to enter the collection cavity.

\* \* \* \* \*